US010653601B2

(12) United States Patent
Hoke, II et al.

(10) Patent No.: US 10,653,601 B2
(45) Date of Patent: May 19, 2020

(54) WATER SOLUBLE SURFACTANT COMPOSITION HAVING IMPROVED TASTE

(71) Applicant: The Procter & Gamble Company, Cincinnati, OH (US)

(72) Inventors: Steven Hamilton Hoke, II, West Chester, OH (US); John Christian Haught, West Chester, OH (US); Marc Alan Hester, Cincinnati, OH (US); Brian David Clair, Ft. Wright, KY (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 14/732,878

(22) Filed: Jun. 8, 2015

(65) Prior Publication Data
US 2015/0265515 A1 Sep. 24, 2015

Related U.S. Application Data

(66) Continuation of application No. 13/564,853, filed on Aug. 2, 2012, now Pat. No. 9,078,826, Substitute for application No. 61/514,198, filed on Aug. 2, 2011.

(51) Int. Cl.
A61K 8/55 (2006.01)
A61K 8/44 (2006.01)
A61Q 11/00 (2006.01)
A61Q 11/02 (2006.01)
A61K 8/41 (2006.01)

(52) U.S. Cl.
CPC ............ A61K 8/55 (2013.01); A61K 8/41 (2013.01); A61K 8/44 (2013.01); A61K 8/556 (2013.01); A61Q 11/00 (2013.01); A61Q 11/02 (2013.01); A61K 2800/596 (2013.01)

(58) Field of Classification Search
None
See application file for complete search history.

(56) References Cited

U.S. PATENT DOCUMENTS

| 4,152,421 | A | 5/1979 | Asakawa et al. | |
|---|---|---|---|---|
| 4,206,198 | A | 6/1980 | Schmolka | |
| 4,352,829 | A | 10/1982 | Noyes et al. | |
| 4,670,575 | A | 6/1987 | Kurosaki et al. | |
| 5,322,643 | A | 6/1994 | Schwartz et al. | |
| 5,807,516 | A | 9/1998 | Cottrell et al. | |
| 7,384,898 | B2 * | 6/2008 | Koshti | C11D 1/94 510/123 |
| 9,078,826 | B2 * | 7/2015 | Hoke, II | A61K 8/44 |
| 2002/0010104 | A1 | 1/2002 | Ewbank et al. | |
| 2007/0004801 | A1 * | 1/2007 | Koshti | A61K 31/205 514/554 |
| 2007/0123445 | A1 | 5/2007 | Tuzi et al. | |
| 2008/0247973 | A1 | 10/2008 | Baig et al. | |
| 2009/0202450 | A1 * | 8/2009 | Prencipe | A61K 8/19 424/50 |
| 2010/0069477 | A1 | 3/2010 | Itoh et al. | |
| 2011/0123462 | A1 * | 5/2011 | Mordas | A61K 8/342 424/49 |

FOREIGN PATENT DOCUMENTS

| EP | 0 658 340 A1 | 6/1995 | |
|---|---|---|---|
| FR | 2 733 982 A1 | 11/1996 | |
| JP | 04-013685 A | 1/1992 | |
| JP | 06-072836 A | 3/1994 | |
| JP | 06-319973 A | 11/1994 | |
| JP | 11-140486 A | 5/1999 | |
| JP | 11-171746 A | 6/1999 | |
| JP | 11-279117 A | 10/1999 | |
| JP | WO 2007122792 A2 * | 11/2007 | ............ A01N 25/30 |
| WO | WO1994/09108 A1 | 4/1994 | |
| WO | WO 1998/26036 A1 | 6/1998 | |
| WO | WO 2000/06690 A1 | 2/2000 | |
| WO | WO 2008/005550 A2 | 1/2008 | |
| WO | WO 2009/062857 A1 | 5/2009 | |
| WO | WO 2011/143312 A1 | 11/2011 | |

OTHER PUBLICATIONS

International Search Report for PCT/US2012/049332, dated Nov. 22, 2012.
International Search Report for PCT/US2012/049314, dated Dec. 10, 2012.
International Search Report for PCT/US2012/049330, dated Jul. 29, 2013.

* cited by examiner

Primary Examiner — Michael P Cohen

(57) ABSTRACT

Treated surfactant composition containing a water-soluble surfactant and exhibiting improved taste, said composition comprising: a water-soluble surfactant selected from alkyl phosphate surfactants, alkyl phosphate ethoxylated surfactants, betaine surfactants, betaine ethoxylated surfactants, amine oxide surfactants, and mixtures thereof and water; wherein the composition further comprises: less than about 4%, by weight of the water-soluble surfactant, of total undesirable non-polar materials; less than about 2.5%, by weight of the water-soluble surfactant, of alcohols having a carbon chain length of greater than 4; less than about 1%, by weight of the water-soluble surfactant, of amine and amide materials; and less than about 1%, by weight of the water-soluble surfactant, undesirable non-polar materials selected from aldehydes, esters, ketones, and organic acids. Such compositions wherein the compositions have been subjected to liquid-liquid extraction processes.

9 Claims, No Drawings

WATER SOLUBLE SURFACTANT COMPOSITION HAVING IMPROVED TASTE

FIELD OF THE INVENTION

The present invention relates to treated surfactant compositions having improved taste, such compositions containing water-soluble surfactant, reduced levels of undesirable non-polar materials, and water.

BACKGROUND OF THE INVENTION

Traditionally, much effort has been expended to improve the taste, color, odor or clarity of oral care compositions such as dentifrice (toothpaste), mouth rinse, and the like. Because of the nature of such compositions, the taste of a product may often be of more importance to consumers than the actual or perceived efficacy. Since many efficacious oral care components have undesirable taste, color, odor or clarity, efforts to improve these characteristics are common in the art. For taste, one way to remedy an undesirable product taste is to add additional components, such as flavors, that will improve the overall taste experience for the consumer. However, such remedies can be expensive and it may be difficult to entirely mask an undesirable taste. Improvement of color or clarity through dyes or other additives has similar issues.

Water-soluble surfactants such as alkyl phosphate surfactants are commercially available for use in a variety of consumer products, including oral care compositions. These anionic surface active organophosphate agents have a strong affinity for enamel surface and have sufficient surface binding propensity to desorb pellicle proteins and remain affixed to enamel surfaces. Such properties make these materials desirable for incorporation in oral care compositions such as toothpaste. However, these materials have not been widely commercialized in oral care compositions, despite their desirable properties. One reason for this lack of commercialization may be the negative taste and/or odor profile commonly associated with commercially available alkyl phosphate materials. Although taste may not be a consideration in other consumer product industries, such as laundry, shampoo or personal cleansing, it is an important consideration in oral care. Similarly, while any undesirable odor associated with materials used in laundry, shampoo or personal cleansing products can typically be remedied by the addition of perfume, perfume levels must be kept to a minimum in oral care compositions for consumer acceptance and could produce further unpleasant tastes when utilized.

Purification of surfactant materials through steam-stripping, vacuum-stripping, and/or carbon filtration processes is also generally known to beneficially remove impurities to increase efficacy, minimize undesirable side reactions, and the like. However, these purification processes have been found to be insufficient to remedy the unpleasant tastes and/or odors associated with commercially available water-soluble surfactant materials.

Liquid/liquid extractions (LLE) are generally known in the art as useful for separating components of a mixture, wherein the constituents have differing polarities which can be separated when mixed within two immiscible solvents that form a liquid bilayer after mixing. For example, LLEs are useful for purifying or cleaning samples which contain impurities of significantly differing polarity than the majority or desirable component(s) of the sample. This can be achieved by mixing a sample with a solvent that is immiscible with the primary liquid in which the sample is dissolved.

LLE has been utilized in chemical processing to reduce or eliminate undesirable by-products or contaminants. For instance, PCT Patent Application WO 2008005550 to Hoke, et al (Procter & Gamble) discloses a water washing procedure to remove polar sulfur impurities from peppermint oils to avoid malodor formation when formulated in dentifrice containing stannous ions. In U.S. Pat. No. 4,352,829 to Noyes, et al (Procter & Gamble) an ethyl acetate extraction of caffeine from coffee was shown to be an effective decaffeination process.

However, there is still an interest in finding ways to improve the overall taste and/or odor of water-soluble surfactants such as those used in an oral care composition that are efficacious, cost-effective, and desirable to consumers.

SUMMARY OF THE INVENTION

It has now surprisingly been found that liquid-liquid extraction processes utilizing solvents such as ethyl acetate may be useful to significantly reduce the occurrence of non-polar materials found in water-soluble surfactant raw materials and thereby improve the surfactant's odor and/or taste profile.

Without being limited by theory, it is now believed that water-soluble surfactants previously generally thought to have bad taste and/or odor profiles stemming from the pure material itself are in fact surprisingly acceptable in terms of taste and odor. It has been surprisingly found that non-polar materials commonly present in commercially available water-soluble surfactant compositions such as residual alcohols, alcohol ethoxylates, aldehydes, ethers, ketones, alkylamines, and esters, may be linked to the majority of the negative taste and odor profiles previously associated with the surfactants themselves. Since some of these materials are often used in flavors and perfumes, it was further surprising that a new process for more efficiently extracting these materials from the underlying surfactant would produce such results. For example, dodecanol and dodecanal are commonly taught to be safe and useful for inclusion in flavors and perfumes, yet it has been surprisingly found that if included in water-soluble surfactant compositions at significantly higher levels, these materials present an unpleasant taste such as bitter, soapy and the like.

Further without being limited by theory, liquid-liquid extraction using the appropriate solvent is more effective than previously known techniques to purify such surfactants, allowing for the incorporation of such surfactants into oral care products with minimal negative taste and/or odor attributes.

The present invention is therefore directed to treated surfactant compositions containing a water-soluble surfactant and exhibiting improved taste, said composition comprising: from about 10% to about 94%, by weight of the composition, of a water-soluble surfactant selected from alkyl phosphate surfactants, alkyl phosphate ethoxylated surfactants, betaine surfactants, betaine ethoxylated surfactants, amine oxide surfactants, and mixtures thereof; and from about 3% to about 90%, by weight of the composition, of water; wherein the composition further comprises: less than about 4%, by weight of the water-soluble surfactant, of total undesirable non-polar materials; less than about 2.5%, by weight of the water-soluble surfactant, of alcohols having a carbon chain length of greater than 4; less than about 1%, by weight of the water-soluble surfactant, of amine and amide materials; and less than about 1%, by weight of the water-soluble surfactant, undesirable non-polar materials selected from aldehydes, esters, ketones, and organic acids.

In one embodiment, the present invention relates to such compositions wherein the water-soluble surfactant is at least about 30% soluble in water.

In one embodiment, the present invention relates to such compositions wherein the water-soluble surfactant is selected from cocoamidopropyl betaines, lauryl betaines, capryl/capramidobetaines, mono alkyl phosphates, alkyl ethoxylated surfactants, amine oxides, and mixtures thereof.

In one embodiment, the present invention relates to such compositions wherein the water-soluble surfactant is selected from cocoamidopropyl betaines, mono alkyl phosphates, alkyl ethoxylated surfactants, and mixtures thereof.

In one embodiment, the present invention relates to such compositions wherein the water soluble surfactant is an ethoxylated mono alkyl phosphate surfactant.

In one embodiment, the present invention relates to such compositions wherein the composition comprises from about 10% to about 50%, by weight of the composition, of water-soluble surfactant.

In one embodiment, the present invention relates to such compositions wherein the composition comprises less than about 2%, by weight of the water-soluble surfactant, of undesirable non-polar materials.

In one embodiment, the present invention relates to such compositions wherein the composition comprises from about 3% to about 20%, by weight of the composition, of water.

In one embodiment, the present invention relates to such compositions wherein the composition comprises less than about 1%, by weight of the water-soluble surfactant, of alcohols having a carbon chain length of greater than 4.

In one embodiment, the present invention relates to such compositions wherein the composition comprises from about 20% to about 30%, by weight of the composition, of the water-soluble surfactant; from about 60% to about 90%, by weight of the composition, of water; and less than about 2%, by weight of the water-soluble surfactant, of total alcohols having a carbon chain length of greater than 4.

In one embodiment, the present invention relates to such compositions wherein the composition has been subjected to a liquid-liquid extraction process.

The present invention further relates to treated surfactant compositions containing a mono alkyl phosphate surfactant and having improved taste, said composition comprising: from about 10% to about 94%, by weight of the composition, of mono alkyl phosphate surfactant; from about 3% to about 90%, by weight of the composition, of water; less than about 4%, by weight of the water-soluble surfactant, of undesirable non-polar materials; and less than about 2.5%, by weight of the water-soluble surfactant, of alcohols having a carbon chain length of greater than 4.

In one embodiment, the present invention relates to such compositions wherein the composition comprises less than about 0.5%, by weight of the mono alkyl phosphate surfactant, of alcohols having a carbon chain length of greater than 4.

In one embodiment, the present invention relates to such compositions wherein the surfactant is selected from cocoamidopropyl betaines and comprises less than about 3%, by weight of the cocoamidopropyl betaine surfactant, of undesirable non-polar materials; and comprises less than about 1%, by weight of the cocoamidopropyl betaine surfactant, of amine and amide materials.

In one embodiment, the present invention relates to such compositions wherein the composition comprises less than about 0.25%, by weight of the cocoamidopropyl betaine surfactant, of amine and amide materials.

The present invention further relates to treated surfactant compositions containing a water-soluble surfactant and having improved taste, said composition consisting essentially of: from about 10% to about 94%, by weight of the composition, of a water-soluble surfactant; from about 3% to about 90%, by weight of the composition, of water; and less than about 1%, by weight of the water-soluble surfactant, of undesirable non-polar materials.

The present invention further relates to oral care compositions comprising such surfactant compositions.

The present invention further relates to such oral care compositions that are in a form selected from toothpaste, dentifrice, tooth gel, subgingival gel, mouthrinse, mousse, foam, mouthspray, lozenge, chewable tablet, chewing gum or denture product.

The present invention further relates to such oral care compositions wherein the oral care composition is incorporated onto strips or films for direct application or attachment to oral surfaces.

DETAILED DESCRIPTION OF THE INVENTION

The present invention relates to treated water-soluble surfactant compositions having improved taste. Such compositions contain from 10% to about 94%, by weight of the composition, of a water-soluble surfactant selected from alkyl phosphate surfactants, alkyl phosphate ethoxylated surfactants, betaine surfactants, betaine ethoxylated surfactants, amine oxide surfactants, and mixtures thereof; and from about 3% to about 90%, by weight of the composition, of water; wherein the composition further comprises: less than about 4%, by weight of the water-soluble surfactant, of total undesirable non-polar materials; less than about 2.5%, by weight of the water-soluble surfactant, of alcohols having a carbon chain length of greater than 4; less than about 1%, by weight of the water-soluble surfactant, of amine and amide materials; and less than about 1%, by weight of the water-soluble surfactant, undesirable non-polar materials selected from aldehydes, esters, ketones, and organic acids.

In one embodiment, the treated water-soluble surfactant composition has been previously subjected to a liquid-liquid extraction process.

These elements will be discussed in more detail below.

Water-Soluble Surfactant

The compositions of the present invention contain from about 10% to about 94%, by weight of the composition of a water-soluble surfactant. In one embodiment, the compositions of the present invention contain from about 10% to about 70%, 10% to about 50%, alternatively from about 20% to about 30%, by weight of the composition, of a water-soluble surfactant.

As used herein "water-soluble surfactant" refers to those surfactants that are at least partially soluble in water, when measured at room temperature (25° C.). In one embodiment, the water-soluble surfactant is at least 10% soluble in water, alternatively is at least 20% soluble in water, and still alternatively is at least 30% soluble in water, alternatively at least 40% soluble in water.

Examples of water-soluble surfactants useful herein include cocoamidopropyl betaines, lauryl betaines, capryl/capramidobetaines, mono alkyl phosphates, alkyl ethoxylated phosphates, amine oxides, and mixtures thereof.

Water-soluble surfactants useful herein may, in some embodiments be selected from anionic surfactants such as alkyl phosphates. These surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

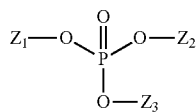

Some other agents include alkyl or alkenyl phosphate esters represented by the following structure:

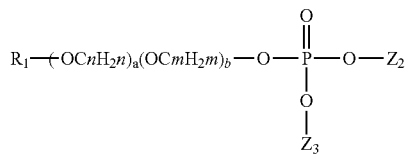

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a (OCmH2m)b- group. Examples of suitable agents include alkyl and alkyl (poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio)acetate, coco betaine or 2-(N-coco-N, N-dimethyl ammonio)acetate, myristyl betaine, palmityl betaine, lauryl betaine, cetyl betaine, stearyl betaine, etc. The amidobetaines are exemplified by cocoamidoethyl betaine, cocoamidopropyl betaine (CAPB), and lauramidopropyl betaine. The unwanted tastes often associated with these surfactants are soapy, bitter, chemical, and/or artificial.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The unwanted tastes often associated with these surfactants are soapy, chemical, and/or artificial.

Water-soluble amphoteric surfactants useful herein further include amine oxide surfactants Amine oxides are the result of oxidation of tertiary amines, typically C12-C18 alkyl dimethyl, N-oxides. For example, amine oxide surfactants useful herein may include lauryl dimethyl amine oxide; lauryl dihydroxyethyl amine oxide; cocamidopropyl amine oxide; Lauramidopropylamine oxide; cetyl dimethyl amine oxide; 3-Lauramidopropyl-N,N-dimethylamine oxide.

In one embodiment, the water-soluble surfactant is selected from alkyl phosphate surfactants, alkyl phosphate ethoxylated surfactants, lauryl sulfate surfactants, betaine surfactants, betaine ethoxylated surfactants, amine oxide surfactants, and mixtures thereof. In another embodiment, the water-soluble surfactant is selected from alkyl phosphate surfactants, alkyl phosphate ethoxylated surfactants, and mixtures thereof. In one embodiment, the water-soluble surfactant is a mono alkyl phosphate surfactant.

In one embodiment, the surfactant is selected from cocoamidopropyl betaines, mono alkyl phosphates, ethoxylated mono alkyl phosphates, and mixtures thereof.

Water

The compositions of the present invention contain from about 3% to about 90%, by weight of the composition, of water. In one embodiment, the composition includes from about 30% to about 90%, by weight of the composition, of water. In one embodiment, the compositions of the present invention contain from about 3% to about 20%, alternatively from about 60% to about 90%, alternatively from about 70% to about 80%, by weight of the composition, of water.

Undesirable Non-Polar Material

The compositions of the present invention contain less than about 4%, by weight of the water-soluble surfactant, of undesirable non-polar materials. The weight of the undesirable non-polar material is measured against the total weight of water-soluble surfactant present in the composition to clearly identify the desired ratio between undesirable non-polar material and water-soluble surfactant and to thereby avoid the dilution effect that may be present with larger amounts of water.

In one embodiment, the composition contains less than about 3%, alternatively less than about 2.5%, alternatively less than about 2%, alternatively less than about 1%, alternatively less than about 0.5%, alternatively less than about 0.25%, alternatively less than about 0.15%, of undesirable non-polar materials, all by weight of the water-soluble surfactant.

In one embodiment, the composition comprises at least 20%, by weight of the composition, of water-soluble surfactant and less than 1%, by weight of the composition, alternatively less than 0.5%, by weight of the composition, of the undesirable non-polar materials.

As used herein "undesirable non-polar materials" refers to any non-polar materials that are found in the water-soluble surfactant composition in need of treatment. In one embodiment, the undesirable non-polar materials are selected from residual alcohols, alcohol ethoxylates, aldehydes, ethers, ketones, alkylamines, amides, amines and esters.

In one embodiment, the undesirable non-polar materials may be off-tasting components selected from impurities, unreacted starting materials, by-products and/or contaminants. Such undesirable non-polar materials may be described by consumers as soapy, bitter, metallic, earthy or dirty, and astringent. Soapy is typically characterized by the presence of dodecanal or dodecanol. Bitter taste may occur in the presence of alkyl amines or alcohols.

The composition further comprises less than about 2.5%, by weight of the water-soluble surfactant, of alcohols having a carbon chain length of greater than 4. In one embodiment, the composition comprises less than about 2%, alternatively less than about 1.5%, alternatively less than about 1%, alternatively less than about 0.75%, alternatively less than 0.5%, alternatively less than 0.25%, alternatively less than 0.1%, alternatively less than 0.05%, alternatively less than 0.01%, by weight of the water-soluble surfactant, of alcohols having a carbon chain length of greater than 4.

The composition further comprises less than about 1%, by weight of the water-soluble surfactant, of amine and amide materials. In one embodiment, the composition comprises less than 0.75%, alternatively less than 0.5%, alternatively less than 0.25%, alternatively less than 0.1%, alternatively less than 0.05%, alternatively less than 0.01%, by weight of the water-soluble surfactant, of amine and amide materials.

The composition further comprises less than about 1%, by weight of the water-soluble surfactant, undesirable non-polar materials selected from aldehydes, esters, ketones, and organic acids. In one embodiment, the composition comprises less than 0.75%, alternatively less than 0.5%, alternatively less than 0.25%, alternatively less than 0.1%, alternatively less than 0.05%, alternatively less than 0.01%, by weight of the water-soluble surfactant, of undesirable non-polar materials selected from aldehydes, esters, ketones, and organic acids.

In one embodiment, the water-soluble surfactant is mono alkyl phosphate. In one such embodiment, the composition comprises mono alkyl phosphate and the composition further contains less than about 2.5%, alternatively less than about 2%, alternatively less than about 1.5%, alternatively less than about 1%, alternatively less than about 0.5%, alternatively less than about 0.1%, alternatively less than about 0.01%, by weight of the mono alkyl phosphate, of alcohols having a carbon chain length greater than 4.

In one embodiment, the water-soluble surfactant is a cocoamidopropyl betaine and the composition contains less than about 1%, alternatively less than about 0.75%, alternatively less than about 0.5%, alternatively less than about 0.1%, alternatively less than about 0.05%, alternatively less than about 0.01%, alternatively no measurable quantity, by weight of the cocoamidopropyl betaine surfactant, of amine and amide materials.

In one embodiment, the composition contains from about 10% to about 50%, alternatively from about 20% to about 30% of the treated water-soluble surfactant, from about 30 to about 70%, alternatively from about 3% to about 30% water, by weight of the composition and less than about 1% total alcohols, by weight of the water-soluble surfactant.

Liquid-Liquid Extraction Process

In one embodiment, the compositions herein have been subjected to a liquid-liquid extraction process. As used herein, liquid-liquid extraction, also known as solvent extraction and partitioning, refers to a standard method to separate compounds based upon their relative solubilities in two different immiscible liquids, here, water and a solvent. It is an extraction of a substance from one liquid phase into another liquid phase. The "liquid-liquid" phrase refers to the two different immiscible liquids that are mixed as part of the extraction procedure. As used herein, immiscible refers to the ability of the two liquids to form at least two layers when mixed together. The layers may be formed after mixing the two liquids and allowing them to sit at rest for a variable period of time, or in some instances, the mixture of the two liquids may be centrifuged and/or cooled below room temperature in order to assist the separation.

Typically in liquid-liquid extraction, one of the phases will be aqueous, and the other a non-polar lipophilic organic solvent such as ether, MTBE, dichloromethane, chloroform, or ethyl acetate. Most organic solvents float on top of an aqueous phase, though important exceptions are most halogenated solvents.

Equipment typically used in a laboratory setting for liquid-liquid extraction includes a separatory funnel. In a small scale plant or lab, batch-wise liquid-liquid extraction methods may be used, such as by mixing the two liquids and then introducing them into a large scale separatory funnel. In larger scale plant production, a multistage continuous counter current extractor may be used to quickly and easily run multiple extractions in sequence. In one embodiment, the process includes the use of a machine selected from centrifugal contactors, thin layer extractors, spray columns, pulsed columns, and mixer-settlers, and combinations thereof, in the extraction process.

In many instances, a separatory funnel has the shape of a cone surmounted by a hemisphere. It has a stopper at the top and stopcock (tap), at the bottom. Separating funnels used in laboratories are typically made from borosilicate glass and their stopcocks are made from glass or PTFE. Typical sizes are between 50 mL and 3 L. In industrial chemistry they can be much bigger and for much larger volumes, centrifuges are used.

To use a separatory funnel, the extraction mixture is introduced into the separatory funnel through the top with the stopcock at the bottom closed. The funnel is then closed and shaken gently by inverting the funnel multiple times. The funnel is then inverted and the tap carefully opened to release excess vapor pressure. The separating funnel is set aside to allow for the complete separation of the phases. The top and the bottom tap are then opened and the two phases are individually released by gravitation and separately captured.

In one embodiment, the liquid-liquid extraction process will use an extraction step in which undesirable non-polar materials are transferred from the aqueous phase to the solvent phase and then optionally followed by a scrubbing stage in which the undesirable non-polar materials are removed from the solvent phase, then optionally followed by a stripping stage in which any water-soluble surfactants or other materials are removed from the solvent phase. The solvent phase may then be treated to make it ready for use again.

In one embodiment, the process includes a step of collecting the water-soluble surfactant from the aqueous phase. In another embodiment, after the step of collecting the water-soluble surfactant from the aqueous phase, the water-soluble surfactant is subjected to one or more of the following:
- a) at least one repeat of the process steps, optionally repeating the steps of the process at least 3 times, optionally repeating the steps of the process at least 4 times, in succession;
- b) a further filtration step, optionally using carbon filtration; and/or
- c) incorporation of the water-soluble surfactant into an oral care composition.

Oral Care Compositions

The treated water-soluble surfactant compositions herein may be incorporated into an oral care composition resulting in an oral care composition having improved taste versus one containing an untreated water-soluble surfactant.

As used herein, "oral care composition" is meant a product, which in the ordinary course of usage, is not intentionally swallowed for purposes of systemic administration of particular therapeutic agents, but rather is retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. The oral care composition may also be incorporated onto strips or films for direct application or attachment to oral surfaces.

In one embodiment, the oral care composition further comprises an abrasive. Examples of abrasives useful herein include precipitated silica, fused silica, and mixtures thereof.

EXAMPLES

Example I

Improved MAP L213/S Surfactant

Undesirable non-polar materials were extracted from MAP L213/S (a mono alkyl phosphate surfactant in aqueous solution, supplied by Rhodia), using the processes set forth herein wherein ethyl acetate (supplied by Honeywell Burdick & Jackson, Muskegon, Mich., USA) was used as the extraction solvent. The extracted materials were then analyzed and the treated MAP L213/S was evaluated for taste and odor after the extraction and shown to be very mild, especially when compared with the starting MAP L213/S material. The undesirable materials removed from the MAP L213/S commercially supplied material are set forth in Table 3, below. The following process steps were taken:
1. 100 grams of MAP L213/S were placed into a clean 250 mL separatory funnel.
2. 100 mL of ethyl acetate was added to the separatory funnel, which was stoppered, and shaken vigorously for approximately 1 minute.
3. The separatory funnel contents were then rested for a period of time until they ettled into two visibly distinct layers.
4. The bottom layer (treated MAP L213/S) was drained from the separatory funnel into a second, clean 250 mL separatory funnel.
5. The ethyl acetate was separately collected and set aside for other purposes.
6. A second aliquot of 100 mL of fresh ethyl acetate was then added to the treated MAP L213/S in the separatory funnel and the steps 2-5 were repeated for a total of 5 times.
7. After the last extraction step, the aqueous layer was collected into a round bottom flask, which was then placed on a rotavapor (model RE111 supplied by BUCHI Labortechnik AG in Flawil, Switzerland). The water bath of the rotavapor was set at 80° C. and allowed to run until the ethyl acetate odor is no longer perceived.
7. The mass of the treated MAP L213/S surfactant was then obtained and water was added to make up for any mass loss due to water loss along with the EtOAc removal. "To assess extraction efficiency, samples of both the pre- and post-extracted oral care component are analyzed via immersion Solid Phase Microextraction (SPME) followed by GC-MS (using an Agilent model 6890 GC & model 5973 Mass Spectrometric Detector, Agilent Technologies, Wilmington, Del. USA). Compare the impurity peak area in the pre- and post-extracted samples to determine the efficiency of their removal."

TABLE 3

Results of Mono alkyl phosphate LLE treatment with EtOAc

| Undesirable Material | Retention Time (Min) | Control (Pre-extract) Peak Area | Post Extract Peak Area | Area Reduction (%) |
|---|---|---|---|---|
| Undecane | 3.39 | 1216114 | 0 | 100.0 |
| Dodecene Isomer | 4.35 | 3218343 | 0 | 100.0 |
| Dodecene Isomer | 4.42 | 3450618 | 0 | 100.0 |
| Dodecene Isomer | 4.46 | 2311369 | 0 | 100.0 |
| Dodecene Isomer | 4.57 | 4329376 | 0 | 100.0 |
| Dodecene Isomer | 4.66 | 2547216 | 0 | 100.0 |
| Tridecene Isomer | 5.09 | 2406145 | 0 | 100.0 |
| Tridecene Isomer | 5.15 | 1220445 | 0 | 100.0 |
| Tridecene Isomer | 5.19 | 438095 | 0 | 100.0 |
| Tridecene Isomer | 5.29 | 1367495 | 0 | 100.0 |
| Tridecene Isomer | 5.38 | 1114436 | 0 | 100.0 |
| Tetradecene Isomer | 5.45 | 674727 | 0 | 100.0 |
| Tetradecene Isomer | 5.52 | 1030783 | 0 | 100.0 |
| Tetradecene Isomer | 5.59 | 1218184 | 0 | 100.0 |
| Tetradecene Isomer | 5.63 | 1589820 | 0 | 100.0 |
| Tetradecene Isomer | 5.77 | 573418 | 0 | 100.0 |
| Tetradecene Isomer | 5.80 | 220422 | 0 | 100.0 |
| Tetradecene Isomer | 5.83 | 184627 | 0 | 100.0 |
| Tetradecene Isomer | 5.88 | 300141 | 0 | 100.0 |
| Tetradecene Isomer | 5.97 | 199647 | 0 | 100.0 |
| Tetradecene Isomer | 5.99 | 175759 | 0 | 100.0 |
| Tetradecene Isomer | 6.06 | 177721 | 0 | 100.0 |
| Pentadecane | 6.22 | 669888 | 0 | 100.0 |
| Methyl 4,6-decadienyl ether | 6.61 | 1023628 | 0 | 100.0 |
| Hexadecane | 6.83 | 1645290 | 0 | 100.0 |
| Dodecanal | 7.57 | 2654710 | 129439 | 95.1 |
| Unknown | 7.60 | 776038 | 0 | 100.0 |
| Unknown | 7.64 | 1108611 | 0 | 100.0 |
| Unknown | 7.70 | 1879031 | 0 | 100.0 |
| Methyl 6,8-dodecadienyl ether | 7.80 | 1223734 | 0 | 100.0 |
| Unknown | 7.84 | 1463962 | 0 | 100.0 |
| Unknown | 7.95 | 3115904 | 0 | 100.0 |
| Butyl-substituted tetrahydrofuran | 8.04 | 5371992 | 0 | 100.0 |
| Branched alcohol | 8.29 | 1323195 | 0 | 100.0 |
| Branched alcohols | 8.38 | 4633193 | 0 | 100.0 |
| Branched alcohols | 8.48 | 8500950 | 0 | 100.0 |
| Dodecanol | 8.88 | 101956289 | 932638 | 99.1 |
| Ethylene glycol monododecyl ether | 10.23 | 55816598 | 522217 | 99.1 |
| Diethylene glycol monododecyl ether | 12.00 | 31588284 | 560933 | 98.2 |
| Triethylene glycol monododecyl ether | 14.90 | 8518697 | 264967 | 96.9 |
| | | | Average % Reduction | 99.7 |

The resulting treated MAP L213/S having a composition according to the present invention was then subjected to comparative taste testing as follows:

The following MAP L213/S compounds (all based upon the MAP L213/S surfactant commercially available from Rhodia) were subjected to a 6 person panel for tasting. Each MAP material was diluted to a level of 1% surfactant in distilled water and neutralized to pH 7. 10 mL samples were provided in 15 mL cups to the panelists. Panelists were instructed to not sample materials more often than once in the morning and once in the afternoon in order to provide enough time for the palate to clear between samples and were instructed to not eat or drink within 15 minutes before sampling. The panelist was instructed to empty the contents of the cup into their mouth without swallowing, swish the product for 10-20 seconds, expectorate, wait 10-20 seconds, and then rate their perceptions for the following categories on a scale of 0 to 60: 1) soapy taste; 2) bitterness amount; 3) other off-taste amount; 4) "soapy taste" intensity; 5) "bitter taste" intensity.

176=Rhodia L213/S, lot SW10G-4636 251=Rhodia L213/S, lot 012
   389=Rhodia L213/S, lot 010
   462=Rhodia L213/S, lot 011
   937=Rhodia L213/S, lot 001 extracted with ethyl acetate pursuant to the process steps set forth above in this Example I Control=Rhodia L213/S, lot 001

As may be seen in Table 4, the control and the comparative examples 176, 251, 389, and 462, all had significantly higher ratings for negative taste elements such as the soapy taste, bitterness amount, other off-taste amount, soapy taste intensity, and bitter taste intensity than the MAP composition treated with ethyl acetate according to the processes set forth herein.

TABLE 4

| Attribute n = 6 | CTL | 176 (Comp) | 251 (Comp) | 389 (Comp) | 462 (Comp) | 937 (Example I) |
|---|---|---|---|---|---|---|
| Soapy Taste | 41.25 | 47.50 | 33.75 | 30.42 | 38.75 | 12.50 |
| Bitterness Amount | 32.50 | 44.08 | 42.08 | 39.58 | 44.58 | 5.83 |
| Other Off-taste Amount | 32.50 | 34.00 | 24.58 | 26.25 | 26.08 | 3.75 |
| "Soapy Taste" Intensity | 42.08 | 45.00 | 32.00 | 28.75 | 39.25 | 7.50 |
| "Bitter Taste" Intensity | 31.25 | 39.17 | 41.25 | 38.75 | 42.92 | 3.17 |

Example II

Improved Cocoamidopropyl Betaine Surfactant

Undesirable non-polar materials were extracted from cocoamidopropyl betaine surfactant, supplied by Stepan, Mexico SA DE CV (Matamoros, MX), using the process steps shown in Example I, except that 20 grams cocoamidopropyl betaine and 20 mL of solvent were used (in place of 100 grams of MAP and 100 mL of solvent) and only 3 repetitions (stages) of steps 2 through 5—substituting the cocoamidopropyl betaine for the MAP L213/S. The extracted materials were then analyzed and the treated cocoamidopropyl betaine surfactant was evaluated for taste and odor after the extraction and shown to be very mild, especially when compared with the starting material. The undesirable materials removed from the commercially supplied material are set forth in Table 5, below.

TABLE 5

Cocoamidopropyl Betaine - Pre and Post 3 Stages of EtOAc Extraction

| Impurity | Retention Time (Min) | Control (Pre-extract) Peak Area | Post Extract Peak Area | Area Reduction (%) |
|---|---|---|---|---|
| Cyclohexyl benzene | 7.43 | 421510 | 0 | 100.0 |
| Dodecanal | 7.57 | 2718310 | 91634 | 96.6 |
| Methyl dodecanoate | 8.04 | 3597403 | 12025 | 99.7 |
| Benzyl alcohol | 8.52 | 11186150 | 370371 | 96.7 |
| Tetradecanal | 8.70 | 396280 | 0 | 100.0 |
| Dodecanol | 8.87 | 1590140 | 319173 | 79.9 |
| Methyl tetradecanoate | 9.11 | 515756 | 0 | 100.0 |
| Biphenyl | 9.19 | 2524375 | 0 | 100.0 |
| Diphenyl ether | 9.28 | 8312954 | 0 | 100.0 |
| Tetradecanol | 9.86 | 264984 | 0 | 100.0 |
| Unknown | 10.16 | 1794756 | 570477 | 68.2 |
| N,N-Dimethyldodecanamide | 10.85 | 737881 | 0 | 100.0 |
| Benzoic Acid | 11.13 | 627445 | 70858 | 88.7 |
| Dodecanoic acid | 11.23 | 7295585 | 295959 | 95.9 |
| N,N-Dimethylpalmitamide | 11.83 | 300264 | 0 | 100.0 |
| Tetradecanoic acid | 12.26 | 2070533 | 93129 | 95.5 |
| Dodecanamide | 12.80 | 378693 | 0 | 100.0 |
| Unknown | 13.66 | 948057 | 515784 | 45.6 |
| Tertiary alkyl dimethylamine | 14.26 | 1761483 | 495040 | 71.9 |
| | | | Average % Reduction | 91.5 |

Example III

Improved Lauryl Betaine Surfactant

Undesirable non-polar materials were extracted from lauryl betaine surfactant, supplied by Mason Chemical Company (Arlington Heights, Ill., USA), using the process steps shown in Example I, substituting the lauryl betaine for the MAP L213/S and only four repetitions of steps (stages) 2 through 5 were completed. The extracted materials were then analyzed and the treated lauryl betaine surfactant was evaluated for taste and odor after the extraction and shown to be very mild, especially when compared with the starting material. The undesirable materials removed from the commercially supplied material are set forth in Table 6, below.

TABLE 6

Lauryl Betaine - Pre and Post 4 Stages of EtOAc Extraction

| Impurity | Retention Time (Min) | Control (Pre-extract) Peak Area | Post Extract Peak Area | Area Reduction (%) |
|---|---|---|---|---|
| Dodecene Isomer | 4.14 | 268607 | 0 | 100.0 |
| Dodecene Isomer | 4.25 | 269099 | 0 | 100.0 |
| Dodecene Isomer | 4.36 | 100143 | 0 | 100.0 |
| Dodecene Isomer | 4.42 | 249301 | 0 | 100.0 |
| Dodecene Isomer | 4.51 | 210691 | 0 | 100.0 |
| Dodecene Isomer | 4.61 | 533604 | 0 | 100.0 |
| Dodecene Isomer | 4.68 | 77816 | 0 | 100.0 |

TABLE 6-continued

Lauryl Betaine - Pre and Post 4 Stages of EtOAc Extraction

| Impurity | Retention Time (Min) | Control (Pre-extract) Peak Area | Post Extract Peak Area | Area Reduction (%) |
|---|---|---|---|---|
| Tertiary Alkyl Dimethyl amine | 5.83 | 119401 | 0 | 100.0 |
| Tertiary Alkyl Dimethyl amine | 6.11 | 110815 | 0 | 100.0 |
| 2-Ethyl-1-hexanol | 6.18 | 197861 | 0 | 100.0 |
| N,N-Dimethyl-1-dodecanamine | 7.05 | 12603358 | 1716473 | 86.4 |
| | | | Average % Reduction | 98.8 |

Example IV

Dentifrice Compositions

Dentifrice compositions according to the present invention are shown below as Examples IVa-IVi in Table 7. These compositions contain surfactants resulting from the process set forth herein in Examples I-III. Such compositions have improved taste versus compositions containing the untreated commercially available water-soluble surfactants.

TABLE 7

Dentifrice Compositions

| Ingredient | IVa | IVb | IVc | IVd | IVe | IVf | IVg | IVh | IVi |
|---|---|---|---|---|---|---|---|---|---|
| Carbomer 956 | 0.2 | | | 0.3 | 0.2 | 0.2 | 0.2 | 0.2 | 0.2 |
| CMC | | 0.75 | 0.2 | | | 1.0 | 1.0 | 1.0 | 1.0 |
| Color Solution (1%) | 0.05 | 0.05 | 0.50 | 0.75 | 0.18 | 0.02 | 0.25 | 0.05 | 0.05 |
| Wintergreen Spice Flavor | | | | | 0.15 | | | | |
| Fruit Mint Flavor | | 0.55 | | | | | | | |
| Mint Flavor | 0.59 | | 0.45 | | 0.42 | 1.0 | 1.2 | 1.0 | 1.0 |
| Cinnamon Flavor | | | | 0.5 | | | | | |
| WS-23 | | | 0.02 | 0.05 | 0.02 | | | | |
| WS-3 | | | 0.02 | 0.05 | 0.02 | | | | |
| MGA | | | | 0.2 | | | | | |
| Menthol | 0.52 | 0.55 | 0.56 | 0.15 | 0.58 | | | | |
| G-180 | 0.01 | 0.03 | 0.015 | 0.004 | 0.01 | 0.01 | 0.03 | 0.008 | 0.02 |
| Potassium Sorbate | | | | | | 0.004 | 0.008 | 0.004 | 0.004 |
| Poloxamer 407 | | | 1.0 | | 0.2 | 0.2 | 0.2 | 0.2 | 0.2 |
| Polyethylene Glycol 300 | 3.0 | 3.0 | | 3.00 | | | | | |
| Polyethylene Glycol 600 | | | 2.3 | | | | | | |
| Propylene Glycol | | | 10.0 | | | | | | |
| Sweetener | 0.46 | 0.5 | 0.45 | 0.4 | 0.58 | 0.4 | 0.4 | 0.4 | 0.4 |
| Silica Abrasive | 22.0 | 31.0 | 20.0 | 21.0 | 17.0 | 15.0 | 15.0 | 15.0 | 15.0 |
| Sodium Benzoate | | | | | | 0.004 | 0.004 | 0.004 | 0.004 |
| Silica Thickening | | | 2.0 | | | 7.0 | 7.0 | 7.0 | 7.0 |
| Sodium Bicarbonate | | 1.50 | 9.0 | | | | | | |
| Sodium Carbonate | | 0.50 | | | | | | | |
| NaOH 50% Soln | | | 1.74 | 2.20 | | 2.0 | 2.0 | 2.0 | 2.0 |
| Na Lauryl Sulfate according to Example IV | 4.0 | 5.0 | 3.0 | 4.0 | 4.0 | | | 3.0 | 2.0 |
| Sodium Fluoride | | | | | | 0.243 | 0.243 | 0.243 | |
| Sodium MFP | 0.76 | 0.76 | 0.76 | 0.76 | 0.76 | | | | 0.76 |
| Glycerin USP 99.7% | 9.0 | 11.9 | 33.0 | 9.0 | | | | | |
| Sorbitol Soln USP | 24.3 | 24.5 | 4.0 | 44.7 | 56.9 | 43.0 | 43.0 | 40.0 | 38.0 |
| Tetra Na Pyrophosphate, Anhydrous | 2.05 | 5.045 | 3.85 | | 3.85 | | | | |
| Tetra Potassium Pyrophosphate (60% Soln) | 6.38 | | | | | | | | |
| Na Acid Pyrophosphate | 2.1 | | | 4.0 | 1.0 | 4.3 | 4.5 | 4.5 | 2.0 |
| Mono Alkyl Phosphate according to Example I | | | | | | 3.5 | 6.7 | 3.5 | 3.5 |
| Cocamidopropyl Betaine (30% soln) according to Example II | | | | | | | 3.5 | | |

TABLE 7-continued

| | Dentifrice Compositions | | | | | | | | |
|---|---|---|---|---|---|---|---|---|---|
| Ingredient | IVa | IVb | IVc | IVd | IVe | IVf | IVg | IVh | IVi |
| Titanium Dioxide | 0.5 | | 1.0 | | 0.25 | 0.3 | 0.3 | 0.2 | 0.2 |
| TiO$_2$/Carnauba Wax Prills | | 0.6 | | 0.3 | | | | | |
| Xanthan Gum | 0.6 | | 0.4 | 0.45 | 0.7 | 0.3 | 0.3 | 0.3 | 0.3 |
| Water | QS | QS | QS | QS | QS | QS | QS | QS | QS |

Example V

Improved Amine Oxide Surfactant

Undesirable non-polar materials were extracted from N,N-Dimethyldodecylamine N-oxide (amine oxide) surfactant (~30% aqueous solution), supplied by Sigma-Aldrich Corporation (St. Louis, Mo., USA), using the process steps shown in Example I, substituting the amine oxide for the MAP L213/S. Additionally, a different rotary evaporator (model EL131 supplied by BUCHI Labortechnik AG in Flawil, Switzerland) was used for removing residual EtOAc. During rotovap, a vacuum was also applied via rough pump (General Electric model SKC36PN435GX, Fort Wayne, Ind., USA), which was controlled by manual adjustment of a clamp added to a teed in segment of hose between the pump inlet and rotovap. Vacuum was increased to the point where surfactant began gentle bubbling. By applying vacuum, the rate of residual EtOAc removal was significantly increased. The pre- and post-extraction amine oxide materials were then analyzed by immersion SPME GC-MS (Agilent model 7890 GC & model 5975 Mass Spectrometric Detector, Agilent Technologies, Wilmington, Del., USA), and the treated amine oxide surfactant was evaluated for taste and odor after the extraction and shown to be very mild, especially when compared with the starting material. GC-MS analyses for this example were performed at a later time with newer equipment and the resulting retention times are slightly longer than for other examples. The undesirable materials removed from the commercially supplied material are set forth in Table 8, below.

TABLE 8

Results for Amine Oxide LLE treatment with EtOAc

| Undesirable Material | Retention Time (Min) | Control (Pre-extract) Peak Area | Post Extract Peak Area | Area Reduction (%) |
|---|---|---|---|---|
| Decane | 3.45 | 729450 | 0 | 100.0 |
| N,N-Dimethylhydroxylamine | 4.198 | 5799292 | 0 | 100.0 |
| Undecane | 4.326 | 1.58E+08 | 0 | 100.0 |
| Undecene Isomer | 4.613 | 2433592 | 0 | 100.0 |
| Undecene Isomer | 4.663 | 514924 | 0 | 100.0 |
| Undecene Isomer | 4.696 | 4576558 | 0 | 100.0 |
| Undecene Isomer | 4.731 | 3314628 | 0 | 100.0 |
| Undecene Isomer | 4.873 | 13478025 | 0 | 100.0 |
| Undecene Isomer | 4.981 | 7185801 | 0 | 100.0 |
| Dodecane | 5.262 | 97542837 | 275259 | 99.7 |
| Dodecene Isomer | 5.517 | 1722855 | 0 | 100.0 |
| Dodecene Isomer | 5.564 | 256787 | 0 | 100.0 |
| Dodecene Isomer | 5.594 | 1970807 | 0 | 100.0 |
| Dodecene Isomer | 5.637 | 1.34E+08 | 20278565 | 84.9 |
| Dodecene Isomer | 5.686 | 1713571 | 0 | 100.0 |
| Dodecene Isomer | 5.749 | 5157893 | 0 | 100.0 |
| Dodecene Isomer | 5.847 | 2337409 | 0 | 100.0 |
| Tridecane | 6.079 | 60387770 | 0 | 100.0 |
| Substituted Tetrahydrofuran | 6.211 | 741293 | 0 | 100.0 |
| Tridecene Isomer | 6.304 | 934388 | 0 | 100.0 |
| Tridecene Isomer | 6.373 | 2370074 | 0 | 100.0 |
| Tridecene Isomer | 6.411 | 1509006 | 0 | 100.0 |
| Tridecene Isomer | 6.514 | 5357518 | 0 | 100.0 |
| Tridecene Isomer | 6.61 | 2493787 | 0 | 100.0 |
| Tetradecane | 6.808 | 88989028 | 0 | 100.0 |
| Tetradecene Isomer | 7.013 | 648872 | 0 | 100.0 |
| Tetradecene Isomer | 7.075 | 793547 | 0 | 100.0 |
| Tetradecene Isomer | 7.119 | 51889810 | 6298997 | 87.9 |
| Methyl Tetradecane Isomer | 7.184 | 1406294 | 0 | 100.0 |
| Tetradecene Isomer | 7.209 | 1387502 | 0 | 100.0 |
| Tetradecene Isomer | 7.301 | 1082259 | 0 | 100.0 |
| Pentadecane | 7.469 | 10662978 | 0 | 100.0 |
| Unknown | 7.683 | 3450057 | 0 | 100.0 |
| Methyl 4,6-decadienyl ether | 7.863 | 19513653 | 0 | 100.0 |
| Hexadecane | 8.094 | 34907941 | 0 | 100.0 |

TABLE 8-continued

Results for Amine Oxide LLE treatment with EtOAc

| Undesirable Material | Retention Time (Min) | Control (Pre-extract) Peak Area | Post Extract Peak Area | Area Reduction (%) |
|---|---|---|---|---|
| Undecanone Isomer | 8.166 | 258835 | 0 | 100.0 |
| N,N-Dimethyl-1-Dodecanamine | 8.304 | 76976187 | 228611 | 99.7 |
| Undecanol | 8.381 | 5483997 | 0 | 100.0 |
| Dimethyl Undecanone | 8.421 | 1533470 | 0 | 100.0 |
| Dodecanone Isomer | 8.582 | 394239 | 0 | 100.0 |
| Heptadecane | 8.681 | 4445134 | 0 | 100.0 |
| Dodecanone Isomer | 8.783 | 537729 | 0 | 100.0 |
| Dodecanal | 8.824 | 16858547 | 3586725 | 78.7 |
| Substituted Tetrahydrofuran | 8.956 | 4420861 | 0 | 100.0 |
| Methyl 6,8-dodecadienyl ether | 9.056 | 13713367 | 0 | 100.0 |
| Octadecane | 9.238 | 23859062 | 0 | 100.0 |
| Dodecanoic acid, methyl ester | 9.303 | 6560940 | 0 | 100.0 |
| N,N-Dimethyl-1-Tetradecanamine | 9.358 | 26094804 | 3499984 | 86.6 |
| Tetradecanone Isomer | 9.737 | 1458218 | 0 | 100.0 |
| Nonadecane | 9.768 | 1489949 | 0 | 100.0 |
| Unknown Amide | 9.864 | 255865 | 0 | 100.0 |
| Tetradecanone Isomer | 9.923 | 589980 | 0 | 100.0 |
| Unknown Amide | 10.048 | 341466 | 0 | 100.0 |
| Dodecanol | 10.137 | 40526459 | 856635 | 97.9 |
| Pentadecanone Isomer | 10.273 | 4602974 | 0 | 100.0 |
| Methyl tetradecanoate | 10.374 | 1435045 | 0 | 100.0 |
| Pentadecanone Isomer | 10.451 | 1668318 | 0 | 100.0 |
| Tetradecanol | 11.128 | 9874928 | 0 | 100.0 |
| N,N-Dimethyldodecanamide | 12.113 | 44118371 | 65123 | 99.9 |
| p-Dicyclohexylbenzene | 12.445 | 2523931 | 0 | 100.0 |
| N,N-Dimethyltetradecanamide | 13.048 | 14118245 | 679312 | 95.2 |
| Dodecanoic acid ester | 14.154 | 24988729 | 0 | 100.0 |
| Dodecanoic acid ester | 15.662 | 2168393 | 0 | 100.0 |
| | | | Avg % Reduction = | 98.9 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 g" is intended to mean "about 20." All percentages, ratios and proportions herein are on a weight basis unless otherwise indicated. Except as otherwise noted, all amounts including quantities, percentages, portions, and proportions, are not intended to indicate significant digits.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Except as otherwise noted, the articles "a", "an", and "the" mean "one or more".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition exhibiting improved taste comprising:
   a. from about 3% to about 20%, by weight of the composition, of water; and b. a surfactant wherein the surfactant comprises cocoamidopropyl betaine, wherein the surfactant comprises less than 1%, by weight of the surfactant, of one or more undesirable materials selected from the group consisting of amines, amides, and combinations thereof; and from 0.01% to 3%, by weight of the surfactant, of a second undesirable material selected from the group consisting of dodecanal, methyl 6,8-dodecadienyl ether, dodecanol, ethylene glycol monodecyl ether, and combinations thereof.

2. The composition according to claim 1 comprising from 0.5% to 1%, by weight of the surfactant, of amine and amide materials.

3. The composition according to claim 1 comprising from 0.01% to 1%, by weight of the surfactant, of aldehydes, esters, ketones, and organic acids.

4. The composition according to claim 1 wherein the surfactant is at least about 30% soluble in water.

5. The composition according to claim 1 wherein the composition is a dentifrice composition.

6. The composition of claim 1 wherein the composition comprises from 0.01% to 0.5%, by weight of the surfactant, of alcohols having a carbon chain length greater than 4.

7. The composition of claim 1 wherein the composition comprises from 0.01% to 0.1%, by weight of the surfactant, of alcohols having a carbon chain length greater than 4.

8. The composition of claim 1 wherein the surfactant is substantially free of dodecene isomers.

9. An oral care composition comprising:
a. from about 3% to about 20%, by weight of the composition, of water; and
b. a surfactant wherein the surfactant comprises cocoamidopropyl betaine; wherein the surfactant comprises
  i. less than 1%, by weight of the surfactant, of one or more undesirable materials selected from the group consisting of amines, and combinations thereof;
  ii. from 0.01% to 1%, by weight of the surfactant, of aldehydes, esters, ketones, and organic acids;
  iii. from 0.15% to 1%, by weight of the surfactant, of amine and amide materials; and
  iv. from 0.01% to 3%, by weight of the surfactant, of a second undesirable material selected from the group consisting of dodecanal, methyl 6,8-dodecadienyl ether, dodecanol, ethylene glycol monodecyl ether, and combinations thereof.

* * * * *